US00PP08466P

United States Patent [19]

VandenBerg

[11] Patent Number: Plant 8,466

[45] Date of Patent: Nov. 16, 1993

[54] CHRYSANTHEMUM PLANT NAMED LAMBADA

[75] Inventor: Cornelis P. VandenBerg, Salinas, Calif.

[73] Assignee: Yoder Brothers, Inc., Barberton, Ohio

[21] Appl. No.: 935,266

[22] Filed: Aug. 27, 1992

[51] Int. Cl.[5] ..... A01H 5/00

[52] U.S. Cl. ..... Plt./82.4

[58] Field of Search ..... Plt./74.1, 82.4

*Primary Examiner*—Howard J. Locker

*Attorney, Agent, or Firm*—Foley & Lardner

[57] ABSTRACT

A Chrysanthemum plant named Lambada particularly characterized by its flat capitulum form; anemone capitulum type; soft pink ray floret color; diameter across face of capitulum of 67 to 83 mm when fully opened, when grown as a single stem spray cut mum; photoperiodic flowering response to short days of 47 to 59 days when grown in Salinas, Calif., and of 59 to 63 days when grown in Bogota, Colombia; plant height of 71 to 87 cm with 11 to 18 long days after planting rooted cuttings prior to start of short days when grown as a single stem cut mum, with no growth regulator applications when grown in Salinas; when grown in Bogota with 14 to 21 long days prior to start of short days plant height is 89 to 107 cm; peduncle length at flowering time of the first lateral after removing the apical bud when grown in Salinas is 8 to 15 cm; peduncle length of the fourth lateral is 10 to 20 cm; when grown in Bogota, peduncle length of the first and fourth lateral is 13 to 18 cm and 18 to 20 cm, respectively; and excellent tolerance to low night temperatures for bud initiation and flower development.

3 Drawing Sheets

The present invention comprises a new and distinct cultivar of Chrysanthemum, botanically known as *Dendranthema grandiflora*, referred to by the cultivar name Lambada.

Lambada, identified as 2493 (88-039001), was originated from a cross made by Cornelis P. VandenBerg in a controlled breeding program in Salinas, Calif., in 1986.

The female parent of Lambada was an unnamed seedling identified as 1443 (83-754009), and described as a flat spooned anemone spray cut mum with a pink ray floret color; a flowering response to short days of 53 to 62 days under normal conditions in Salinas, Calif.; a plant height of 69 to 84 cm with 14 to 15 long days after planting rooted cuttings prior to start of short days; peduncle length of the first lateral after removing the apical bud of 8 to 10 cm, and peduncle length of the fourth lateral of 13 to 18 cm when grown in Salinas. Diameter of capitulum was not recorded. The female parent was discarded in June 1988.

The male parent of Lambada was an unnamed seedling, identified as 5792 (83-446003) and described as a flat display spray cut mum with a white with pink overcast ray floret color; a flowering response to short days of 56 to 63 days under normal conditions in Salinas, Calif.; a plant height of 86 to 102 cm with 6 to 15 long days after planting rooted cuttings prior to start of short days; peduncle length of the first lateral after removing the apical bud of 15 cm, and peduncle length of the fourth lateral of 20 to 23 cm when grown in Salinas. Diameter of capitulum was not recorded. The male parent was discarded on May 4, 1987.

Lambada was discovered and selected as one flowering plant within the progeny of the stated cross by Cornelis P. VandenBerg in August 1988, in a controlled environment in Salinas, Calif.

The first act of asexual reproduction of Lambada was accomplished when vegetative cuttings were taken from the initial selection in November 1988 in controlled environment in Salinas, Calif., by technicians working under supervision of Cornelis P. VandenBerg.

Horticultural examination of controlled flowerings of successive plantings has shown that the unique combination of characteristics as herein disclosed for Lambada are firmly fixed and are retained through successive generations of asexual reproduction.

Lambada has not been observed under all possible environmental conditions. The phenotype may vary significantly with variations in environment such as temperature, light intensity and daylength without, however, any variation in genotype.

The following observations, measurements and comparisons describe plants grown in Salinas, Calif. and in Bogota, Colombia under greenhouse conditions which approximate those generally used in commercial greenhouse practice.

The following traits have been repeatedly observed and are determined to be basic characteristics of Lambada, which, in combination, distinguish this Chrysanthemum as a new and distinct cultivar:

1. Flat capitulum form.
2. Anemone capitulum type.
3. Soft pink ray floret color.
4. Diameter across face of capitulum of 67 to 83 mm when fully opened, when grown as a single stem spray cut mum.
5. Photoperiodic flowering response to short days of 47 to 59 days when grown in Salinas, Calif., and of 59 to 63 days when grown in Bogota, Colombia.
6. Plant height of 71 to 87 cm with 11 to 18 long days after planting rooted cuttings prior to start of short days when grown as a single stem cut mum, with no growth regulator applications when grown in Salinas. When grown in Bogota with 14 to 21 long days prior to start of short days plant height is 89 to 107 cm.

7. Peduncle length at flowering time of the first lateral after removing the apical bud when grown in Salinas is 8 to 15 cm; peduncle length of the fourth lateral is 10 to 20 cm; when grown in Bogota, peduncle length of the first and fourth lateral is 13 to 18 cm and 18 to 20 cm, respectively.
8. Excellent tolerance to night temperatures as low as 5°-10° C. for bud initiation and flower development.

The accompanying photographic drawings show typical inflorescence and leaf characteristics of Lambada, with the colors being as nearly true as possible with illustrations of this type.

Sheet 1 is a color photograph of a side view of Lambada grown as a single stem cut mum.

Sheet 2 is a black and white photograph of three views of the inflorescence of Lambada.

Sheet 3 is a black and white photograph showing the upper and under sides of the leaves of Lambada at 3 stages of development (mature, intermediate and immature). In sheets 2 and 3 a measuring tape in centimeters has been aded.

No commercial cultivar known to the inventor is similar in comparison to Lambada. The combination of the soft pink ray floret color, flat anemone capitulum form and type, and excellent low night temperature tolerance for bud initiation and flower development in unique, and is not represented in any cultivar known to the inventor.

In the following description color references are made to The Royal Horticultural Society Colour Chart. The color values were determined on plant material grown as a single stem spray cut mum in Salinas, Calif. on Mar. 25, 1992.

Classification:

*Botanical.*—*Dendranthema grandiflora* cv Lambada.

*Commercial.*—Anemone spray cut mum.

INFLORESCENCE

A. Capitulum:

*Form.*—Flat.

*Type.*—Daisy.

*Diameter across face.*—67 to 83 mm when fully opened.

B. Corolla of ray florets:

*Color (general tonality from a distance of three meters).*—Soft pink.

*Color (upper surface).*—75B.

*Color (under surface).*—75C.

*Shape of petals.*—Straight, oblong, ribbed.

C. Corolla of disc florets:

*Color (mature).*—Yellow, overlaid with 145A.

*Color (immature).*—Closest to 144B.

D. Reproductive organs:

*Androecium.*—Present on disc florets only; moderatel pollen.

*Gynoecium.*—Present on both ray and disc florets.

PLANT

A. General appearance:

*Height.*—71 to 87 cm when grown as a single stem spray cut mum with 11 to 18 long days after planting rooted cuttings prior to start of short days, with no growth regulator applications when grown in Salinas, Calif. When grown in Bogota, Colombia with 14 to 21 long days prior to start of short days, plant height ranges from 89 to 107 cm.

B. Foliage:

*Color l (upper surface).*—147A.

*Color (under surface).*—147B.

*Shape.*—See photograph.

I claim:

1. A new and distinct Chrysanthemum plant named Lambada, as described and illustrated.

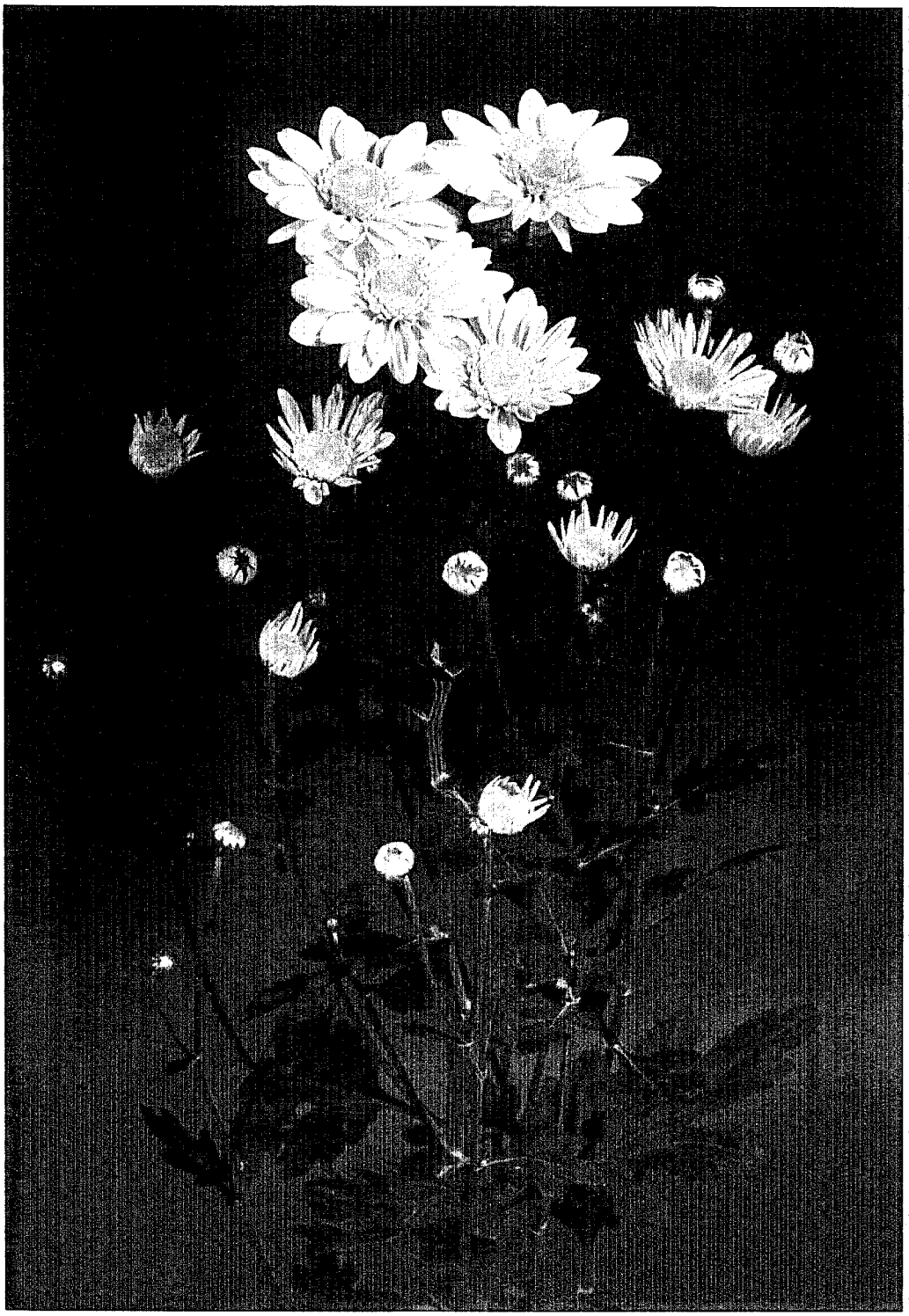

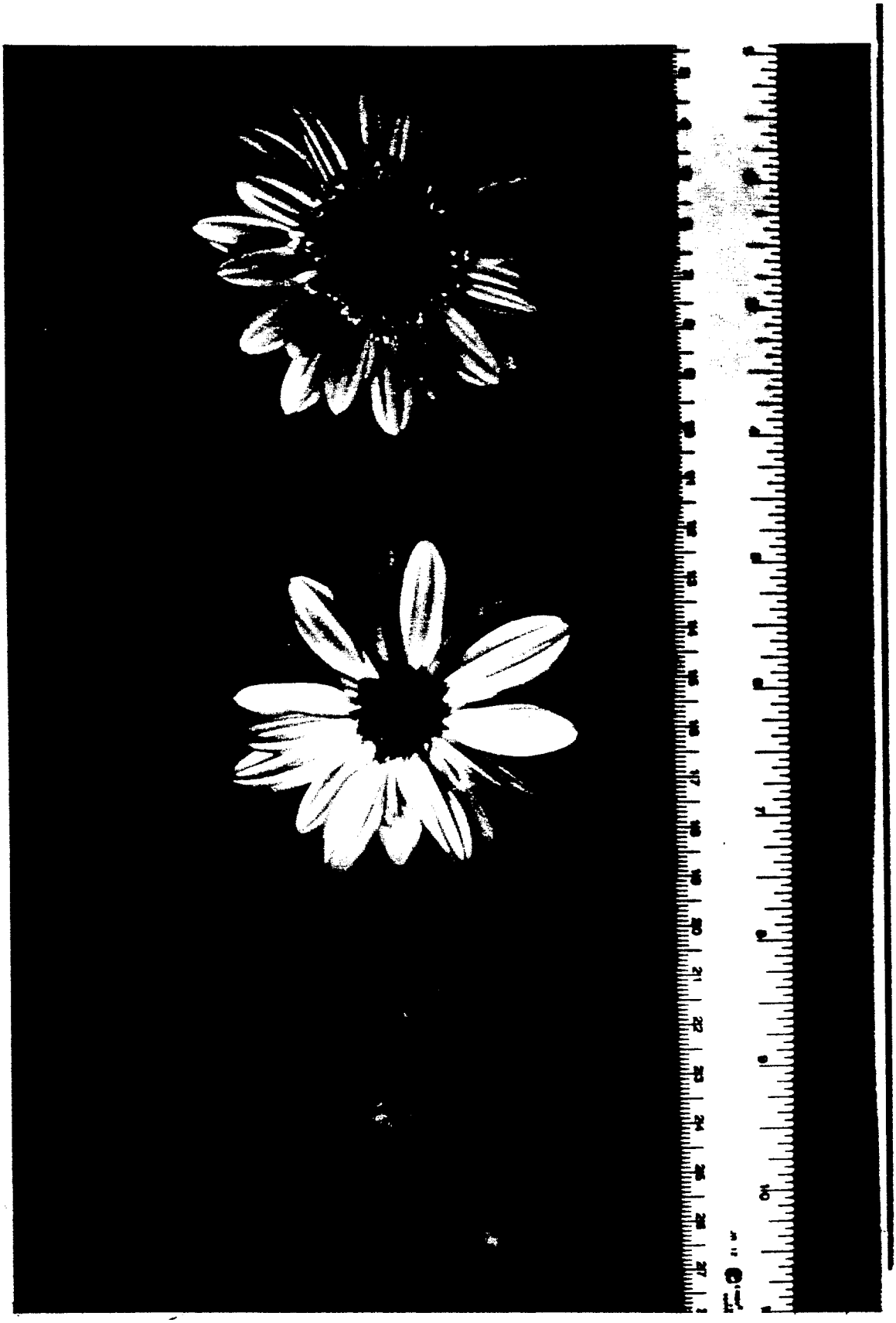

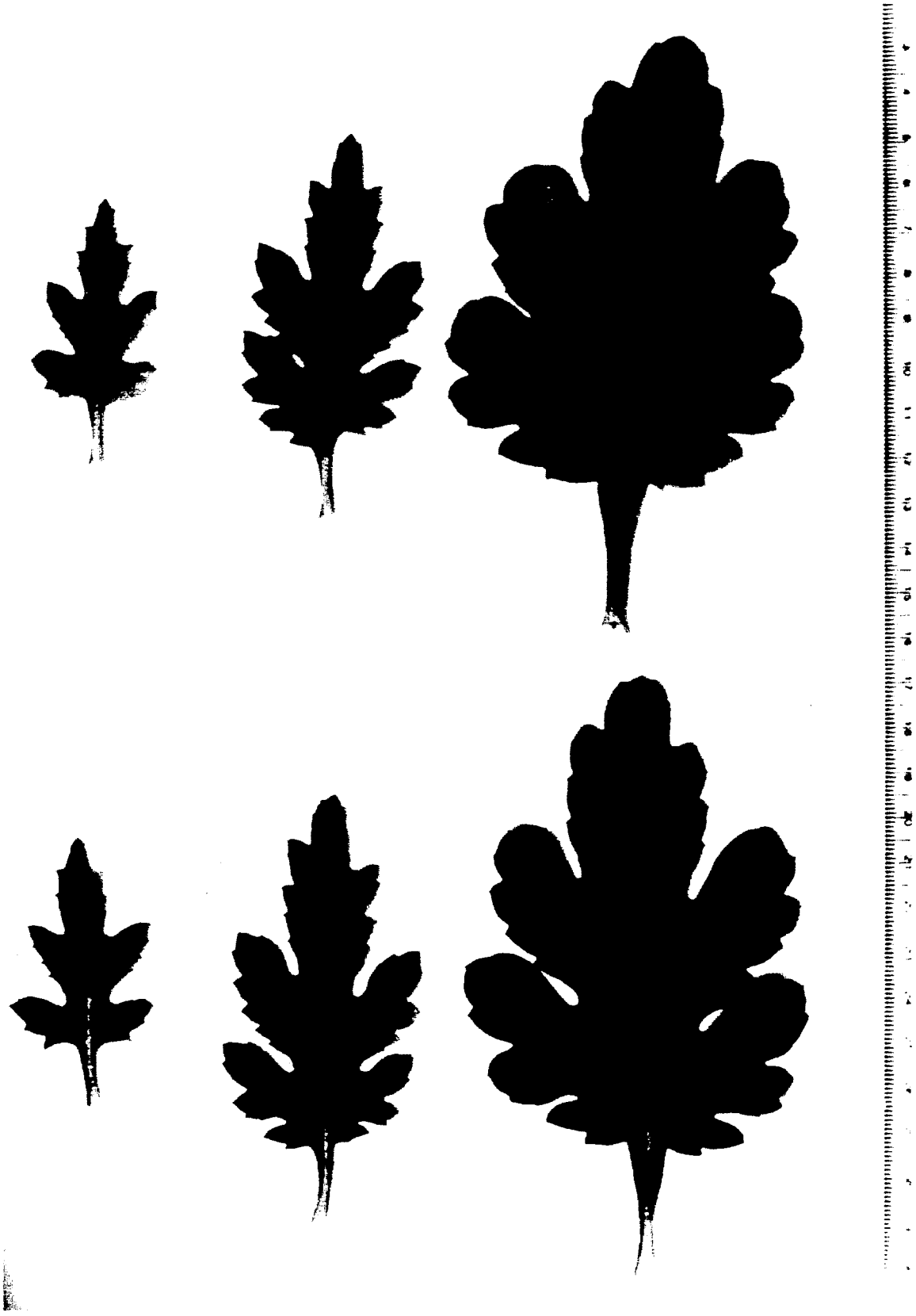

* * * * *